(12) United States Patent
Hu et al.

(10) Patent No.: US 7,977,483 B2
(45) Date of Patent: Jul. 12, 2011

(54) PROCESS FOR MAKING TOPOTECAN

(75) Inventors: Tsung-Cheng Hu, Yongjing Township, Changhua County (TW); Piin-Jye Harn, Tainan (TW)

(73) Assignee: Scinopharm Taiwan, Ltd., Tainan County (TW)

( * ) Notice: Subject to any disclaimer, the term of this patent is extended or adjusted under 35 U.S.C. 154(b) by 726 days.

(21) Appl. No.: 12/082,162

(22) Filed: Apr. 9, 2008

(65) Prior Publication Data

US 2009/0221826 A1 Sep. 3, 2009

Related U.S. Application Data

(60) Provisional application No. 60/922,918, filed on Apr. 11, 2007.

(51) Int. Cl.
*C07D 491/22* (2006.01)
*C07D 491/147* (2006.01)
(52) U.S. Cl. .......................... 546/48; 546/47
(58) Field of Classification Search .............. 546/48, 546/47
See application file for complete search history.

(56) References Cited

U.S. PATENT DOCUMENTS

| 5,004,758 | A | 4/1991 | Boehm et al. |
| 5,734,056 | A | 3/1998 | Burk et al. |
| 6,660,861 | B1 | 12/2003 | Puri et al. |
| 7,547,785 | B2 * | 6/2009 | Palle et al. ............ 546/48 |

FOREIGN PATENT DOCUMENTS

WO    WO/2005046608    5/2005

OTHER PUBLICATIONS

L.A. Paquett: "Encyclopedia of reagents for organic synthesis" Jan. 1, 1995, vol. 3, p. 2090-2093. XP-002575696.
Chen et al., Studies on the polymorph of topotecan hydrochloride and its stability In: Zhongguo Shenghua Yaowu Zazhi, 2005, 26(5), p. 279-281.
Vogt et al., A study of variable hydration states in topotecan hydrochloride In: Journal of Pharmaceutical and Biomedical Analysis, 2006, 40(5), p. 1080-1088.

* cited by examiner

*Primary Examiner* — Charanjit S Aulakh
(74) *Attorney, Agent, or Firm* — Cohen Pontani Lieberman & Pavane LLP

(57) ABSTRACT

A process of making topotecan or a pharmaceutically acceptable salt thereof comprising reacting an iminium salt with 10-hydroxy-camptothecin.

17 Claims, No Drawings

PROCESS FOR MAKING TOPOTECAN

RELATED APPLICATIONS

This application claims priority from U.S. Provisional Patent Application Ser. No. 60/922,918 which was filed on Apr. 11, 2007. The entire content of U.S. Provisional Patent Application Ser. No. 60/922,918 is incorporated herein by reference.

BACKGROUND OF THE INVENTION

1. Field of the Invention

The present invention relates to the preparation of topotecan or pharmaceutically acceptable salt thereof from 10-hydroxycamptothecin.

2. Description of the Related Art

U.S. Pat. No. 5,004,758 discloses topotecan, (S)-10-[(dimethylamino)methyl]-4-ethyl-4,9-dihydroxy-1H-pyrano[3',4': 6,7]-indolizino[1,2-b]quinoline-3,14(4H,12H)dione monohydrochloride (also known as 9-dimethylaminomethyl-10-hydroxycamptothecin, etc.). It has the following structural formula:

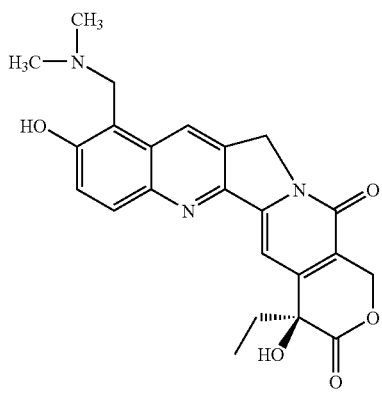

Topotecan hydrochloride for injection is marketed in the U.S. as a cancer chemotherapeutic agent, having the trade name HYCAMTIN®.

The conventional process for making topotecan is by a Mannich reaction of 10-hydroxy-camptothecin. For example, U.S. Pat. No. 5,734,056 discloses the reaction of bis(dimethylamino)methane; bis(N-morpholino)methane; bis(N-methylpiperazinyl)methane; bis(4'-piperidinopiperidinyl)methane; bis(cyclopropylamino)methane; bis(N-methylanilino)methane; or bis(cyclohexylamino)methane with 10-hydroxy-camptothecin to produce 9-substituted camptothecins, which include topotecan.

There is still a need to develop a simple, commercially feasible process of making topotecan or pharmaceutically acceptable salt thereof that has fewer impurities present.

SUMMARY OF THE INVENTION

We have discovered that topotecan or a pharmaceutically acceptable salt thereof can be advantageously produced by reacting 10-hydroxy-camptothecin with an iminium salt of formula (I):

$[H_2C=NR^1R^2]^+X$     (I)

wherein $R^1$ and $R^2$ represent a methyl group or a $CH_2R^3$ group, $R^3$ represents a protective group; X represents an anion;
in the presence of a base and an organic solvent.

The anion may be selected from the group consisting of halogen, mesylate, tosylate, brosylate, nosylate, and triflate.

The base may be an organic or inorganic base or mixture thereof. The organic base may be selected from amine, pyridine, picoline, quinoline, piperidine, pyrrolidine, N-methylmorpholine, and combinations thereof. The inorganic base may be selected from the group consisting of alkali hydroxide, alkali carbonate, alkali bicarbonate, and combinations thereof. Preferably, the base is triethylamine.

The protective group is preferably a halogen or a trimethylsilyl group.

The iminium salt is preferably N,N-dimethylmethyleneiminium halide, more preferably, N,N-dimethylmethyleneiminium chloride or N,N-dimethylmethyleneiminium iodide.

The organic solvent may be selected from the group consisting of an organic halide solvent, ketone, nitrile, alcohol, ester, ether, dipolar aprotic solvent; and combinations thereof. Preferably, the organic solvent is an organic halide solvent selected from C1-C4 chlorinated hydrocarbons, or an alcohol selected from C1-C6 alcohols. More preferably, the organic solvent system is a mixture of dichloromethane and isopropanol.

The reacting step is preferably carried out under anhydrous condition.

The pharmaceutically acceptable salt of topotecan is preferably topotecan hydrochloride, and the process described above further comprises a step of reacting the topotecan with hydrochloric acid (HCl-water or HCl-organic solvent) to make topotecan hydrochloride. Alternatively, topotecan hydrochloride can also be prepared by adding hydrochloric acid to the resulting mixture of the Mannich reaction of 10-hydroxy-camptothecin and the iminium salt of formula (I).

The process in accordance with the present invention can be conducted under anhydrous condition, therefore avoiding the formation of "hydroxymethyl" impurity (MW=394) of formula II:

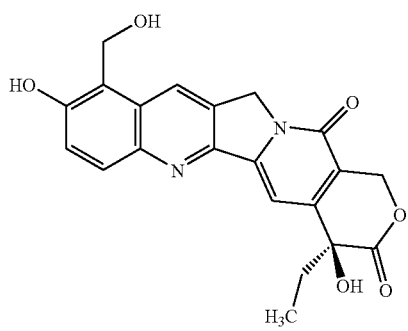

which is evident with known processes for making topotecan. Therefore, topotecan or topotecan salt prepared in accordance with the present invention can be substantially free of any hydroxymethyl impurity of formula II. The term "substantially free" means that the amount of hydroxymethyl impurity of formula II is less than 0.10%, based on the total weight of the final topotecan or topotecan salt product. More preferably, the final topotecan or topotecan salt product is free of any hydroxymethyl impurity of formula II.

In addition, using the bis-amine compounds disclosed in U.S. Pat. No. 5,734,056 to react with 10-hydroxy-camptothecin for the production of topotecan forms the side product carried over from the bis-amine compounds (e.g. dimethylamino will be formed if bis(dimethylamino)methane is used in the this reaction). Furthermore, in the prior art, when amine is applied in the Mannich reaction, an effective amount of strong acid as a catalyst need to be added. However, it is unnecessary to add any acid to catalyze the Mannich reaction disclosed in the present invention.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are merely intended to conceptually illustrate the structures and procedures described herein.

DETAILED DESCRIPTION OF THE PRESENTLY PREFERRED EMBODIMENTS

The following are examples of the process for making topotecan and topotecan hydrochloride in accordance with two embodiments of the present invention.

Example 1

10-hydroxy-camptothecin (1.0 kg), dichloromethane (about 13 kg) and isopropanol (about 8 kg) were charged into a suitable reactor. N,N-dimethylmethyleneiminium chloride (0.3-0.5 kg) was added into the reactor. Triethylamine (0.04-0.2 kg) was then added into the resulting mixture at 20-35° C. and stirred at 20-35° C. for at least 12 hours. When the reaction was complete, a mixture of hydrochloric acid (32%, 0.06-0.3 kg) and isopropanol (about 5 kg) was added into the resulting mixture. After the addition was completed, the resulting mixture was stirred, filtered, and then washed with dichloromethane (about 3 kg). The wet solids were dried to give about 1.5 kg of crude topotecan HCl.

The following is the synthetic route of the reaction described above.

Step 1a: Mannich Reaction

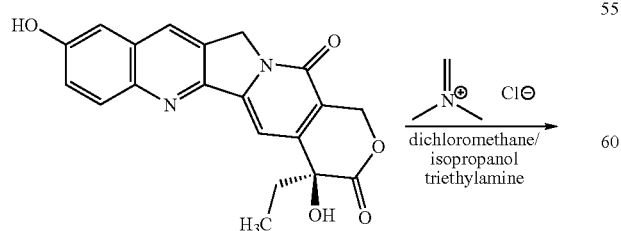

Chemical Formula: $C_{20}H_{16}N_2O_5$
Molecular Weight: 364.35
10-Hydroxy-camptothecin

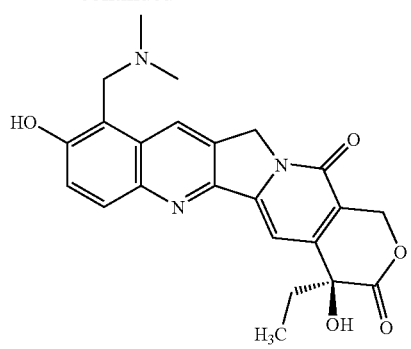

Chemical Formula: $C_{23}H_{23}N_3O_5$
Molecular Weight: 421.45
Topotecan free base Step 1b: Salt Formation

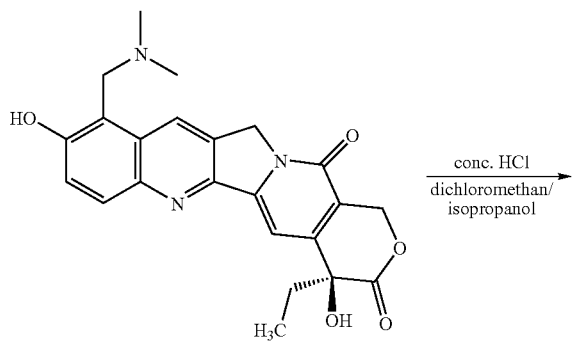

Chemical Formula: $C_{23}H_{23}N_3O_5$
Molecular Weight: 421.45
Topotecan free base

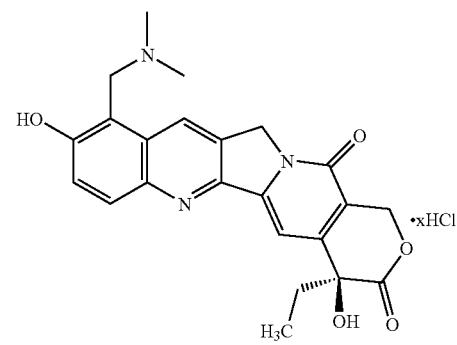

Chemical Formula: $C_{23}H_{23}N_3O_5$
Molecular Weight: 421.45
Topotecan hydrochloride
note: x = 1.0-1.5

Without intent of being bound by any theory, the following is presented for illustration of possible mechanism of the reaction described above.

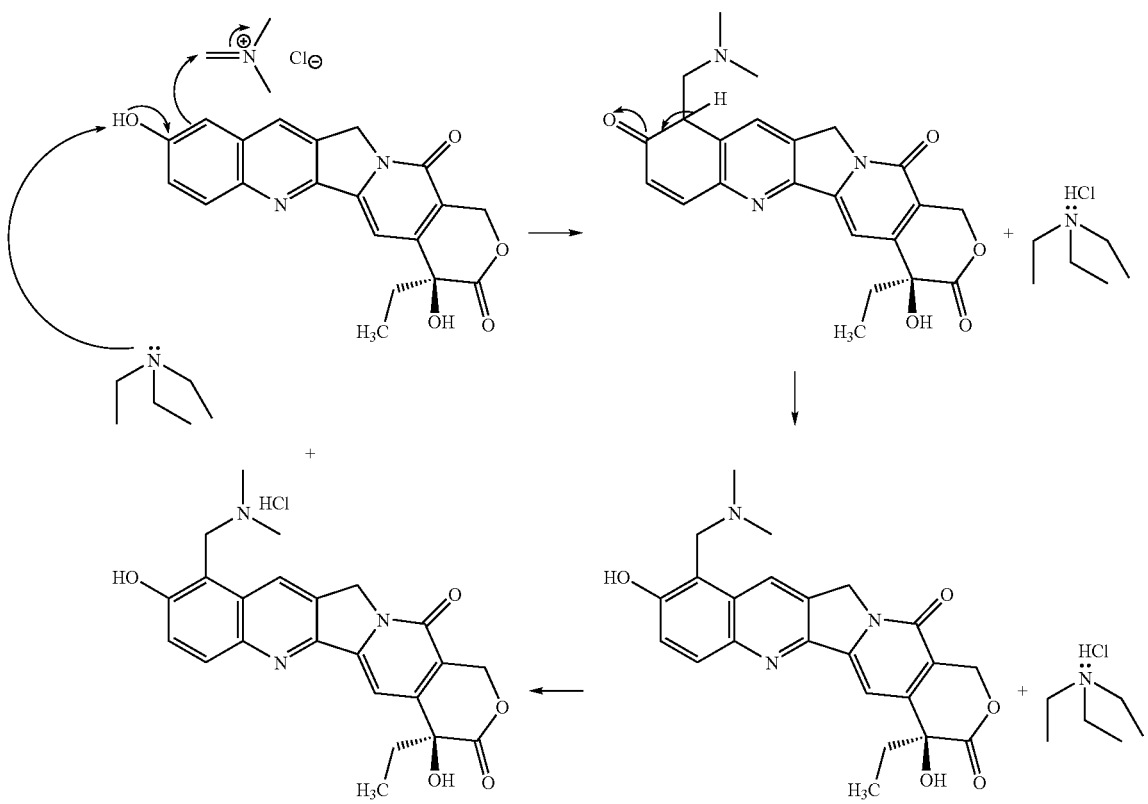

The function of triethylamine is probably to catch the proton in hydroxyl group at C10 of 10-hydroxy-camptothecin. It probably works like a catalyst in this way. In addition to that, triethylamine may function as a base to combine with the HCl. Thus, triethylamine probably serves a number of functions in this reaction.

Example 2

10-hydroxy-camptothecin (0.1 g), N,N-dimethylmethyleneiminium iodide (about 0.06 g), dichloromethane (about 1.3 g), and isopropanol (about 0.8 g) were charged into a suitable reactor. The resulting mixture was stirred for 5-10 minutes. Then triethylamine (0.002-0.03 g) was added, and the resulting mixture was stirred at room temperature. After the reaction was complete, the mixture of hydrochloride acid (37%, 0.003-0.045 g) and isopropanol (about 0.14 g) was added to the resulting mixture. The resulting mixture was stirred over 4 hours, and then the solid was filtered, washed with dichloromethane (about 1 g) and dried under vacuum to give about 0.11 g of topotecan HCl.

The invention is not limited by the embodiments described above which are presented as examples only but can be modified in various ways within the scope of protection defined by the appended patent claims.

We claim:

1. A process for preparing topotecan or a pharmaceutically acceptable salt thereof, comprising reacting 10-hydroxy-camptothecin with an iminium salt of formula (I):

[H$_2$C=NR$^1$R$^2$]$^+$X    (I)

wherein R$^1$ and R$^2$ represent a methyl group or a CH$_2$R$^3$ group, R$^3$ represents a protective group; X represents an anion;

in the presence of a base and an organic solvent.

2. The process of claim 1 wherein the anion is selected from the group consisting of halogen, mesylate, tosylate, brosylate, nosylate, and triflate.

3. The process of claim 1 wherein the base is an organic base selected from the group consisting of amine, pyridine, picoline, quinoline, piperidine, pyrrolidine, N-methylmorpholine, and combinations thereof.

4. The process of claim 1 wherein the base is an inorganic base selected from the group consisting of alkali hydroxide, alkali carbonate, alkali bicarbonate, and combinations thereof.

5. The process of claim 1 wherein the base is triethylamine.

6. The process of claim 1 wherein the protective group is a halogen or a trimethylsilyl group.

7. The process of claim 1 wherein the iminium salt is N,N-dimethylmethyleneiminium halide.

8. The process of claim 7 wherein the N,N-dimethylmethyleneiminium halide is N,N-dimethylmethyleneiminium chloride.

9. The process of claim 7 wherein the N,N-dimethylmethyleneiminium halide is N,N-dimethylmethyleneiminium iodide.

10. The process of claim 7 wherein the reacting step is carried out under anhydrous condition.

11. The process of claim 1, wherein the organic solvent is selected from the group consisting of an organic halide solvent, ketone, nitrile, alcohol, ester, ether, dipolar aprotic solvent; and combinations thereof.

12. The process of claim 11 wherein the organic halide solvent is a C1-C4 chlorinated hydrocarbon.

13. The process of claim 11 wherein the alcohol is a C1-C6 alcohol.

14. The process of claim 1, wherein the organic solvent system is a mixture of dichloromethane and isopropanol.

15. The process of claim 1 where the pharmaceutically acceptable salt of topotecan is topotecan hydrochloride, and the process further comprises a step of reacting the topotecan or the resulting mixture of the reacting step with a hydrochloric acid to make the topotecan hydrochloride.

16. The process of claim 1 wherein the organic solvent is an alcohol.

17. The process of claim 16 wherein the alcohol a C1-C6 alcohol.

* * * * *